United States Patent [19]

Murphy

[11] Patent Number: 5,322,800
[45] Date of Patent: Jun. 21, 1994

[54] METHOD AND DEVICE FOR SAFELY PRESERVING AQUEOUS FIELD SAMPLES USING ACID OR BASE

[75] Inventor: Andrew P. Murphy, Littleton, Colo.

[73] Assignee: The United States of America as represented by the Secretary of the Interior, Washington, D.C.

[21] Appl. No.: 105,560

[22] Filed: Aug. 13, 1993

Related U.S. Application Data

[63] Continuation of Ser. No. 721,805, Jun. 26, 1991, abandoned.

[51] Int. Cl.$^5$ .................. G01N 1/00; B01L 11/00
[52] U.S. Cl. .................. 436/176; 210/263; 210/266; 210/282; 210/416.1; 210/638; 210/660; 422/101; 422/102; 436/177; 436/178
[58] Field of Search .......... 210/263, 266, 282, 416.1, 210/638, 660, 681, 683; 422/40, 41, 101, 102; 436/176–178

[56] References Cited

U.S. PATENT DOCUMENTS

| | | | |
|---|---|---|---|
| 2,775,564 | 12/1956 | Jong | 210/683 |
| 2,898,310 | 8/1959 | Greer | 210/683 |
| 3,340,873 | 9/1967 | Solowey | 604/87 |
| 3,354,883 | 11/1967 | Southernland | 604/88 |
| 3,446,965 | 5/1969 | Ogier et al. | 250/428 |
| 3,519,390 | 7/1970 | Dickey et al. | 210/282 X |
| 3,563,240 | 2/1971 | Silver | 128/234 |
| 3,645,682 | 2/1992 | Cochran | 423/21.1 |
| 3,865,548 | 2/1975 | Padawer | 436/99 |
| 4,086,058 | 4/1978 | Penpleton | 436/164 |
| 4,254,082 | 3/1981 | Schick et al. | 422/59 X |
| 4,309,286 | 6/1982 | Lenihan, Jr. et al. | 210/198.2 |
| 4,341,635 | 7/1982 | Golias | 210/656 |
| 4,797,369 | 1/1989 | Mintz | 436/69 |
| 4,892,710 | 1/1990 | Wong et al. | 422/102 |
| 4,965,061 | 10/1990 | Berry et al. | 210/683 X |

FOREIGN PATENT DOCUMENTS

| | | | |
|---|---|---|---|
| 0021393 | 6/1976 | Japan | 422/59 |
| 1459688 | 2/1989 | U.S.S.R. | |

Primary Examiner—James C. Housel
Assistant Examiner—Milton I. Cano
Attorney, Agent, or Firm—E. Philip Koltos

[57] ABSTRACT

This invention concerns a method and apparatus for collecting and preserving field water samples on site in which a salt solution, contained in a syringe by a rupturable thin film membrane, is injected through a strong acid or base ion exchange filter to produce a required amount of either nitric acid, sulfuric acid or sodium hydroxide for sample collection and preservation.

6 Claims, 1 Drawing Sheet

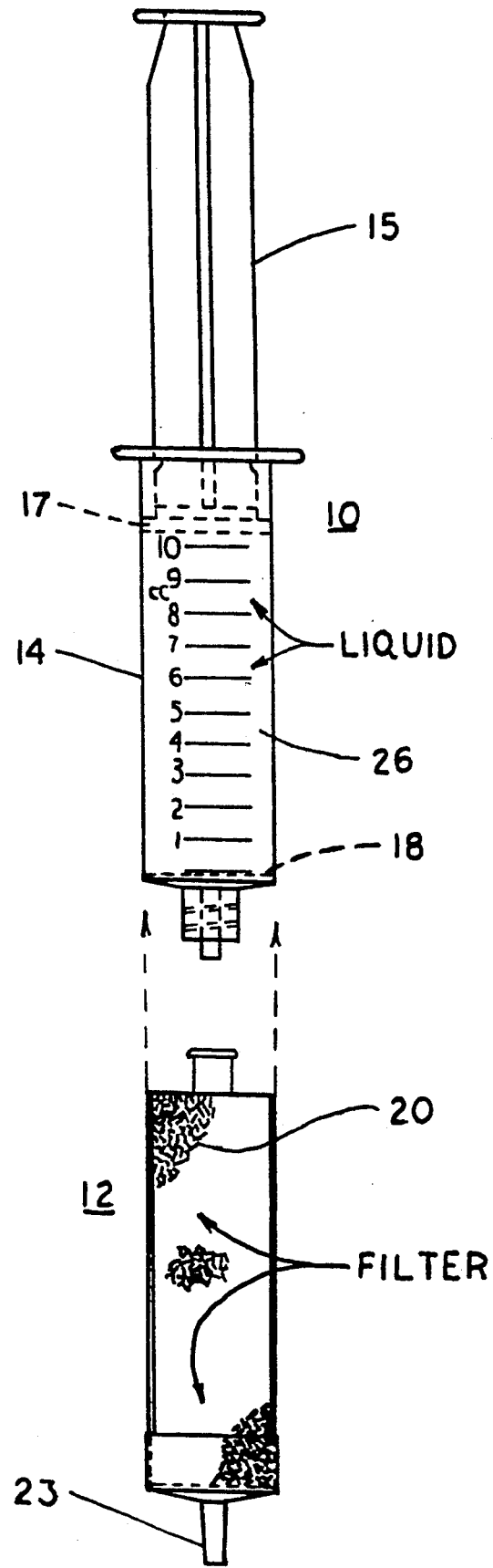

METHOD AND DEVICE FOR SAFELY PRESERVING AQUEOUS FIELD SAMPLES USING ACID OR BASE

RELATED APPLICATION

This application is a continuation of patent application Ser. No. 07/721,805, filed Jun. 26, 1991.

This invention concerns in general a method and apparatus for collecting and preserving field water samples on site and more particularly to a method for safely preserving such samples which includes the selective use of either a strong acid or a strong base ion exchange resin, and to an apparatus for accomplishing the method which comprises a syringe containing a salt solution followed by a strong acid or a strong base ion exchange resin filter.

DESCRIPTION OF THE PRIOR ART

Field water samples in the United States currently are collected for, among other reasons, a determination of hardness, the presence and amount of heavy metals either dissolved or suspended, and the presence of mercury. These samples require the use of nitric acid for preservation. Other samples are collected to determine the presence and amount of phosphorous, either hydrolyzable or dissolved, and of ammonia, nitrate, COD (chemical oxygen demand), oil and grease, organic carbon and phenolics. The latter samples require the use of sulfuric acid for preservation. Samples collected to determine the presence of cyanides require the use of sodium hydroxide for preservation.

Present methods and apparatus for preserving field water samples require the addition of either an acid or a base to field sample containers-either prior to on site collection or on site using pipettes to draw reagents from relatively large bottles or having on hand small glass vials containing the reagents. These procedures have several disadvantages some of which are leakage of reagent during transport, inability to rinse containers on site, photodegradation, and shipping requirements. Further disadvantages related to field additions of acid or base are the danger of containers being broken, the requirement of cumbersome safety equipment, and contamination from contact with the equipment, among other problems.

Examples of prior art methods and apparatus may be found in U.S. Pat. Nos. 4,775,482 and 4,411,796. These patents concern, respectively, a device and method for use in defoaming and/or removing certain impurities from a fluid stream, and the preparation of a novel polyaminic resin which is useful for the extraction of a component having a particular chemical structure e.g., heperin, by means of ionic exchange. A third U.S. Pat. No. 3,340,873, discloses a syringe apparatus having a very thin rupturable diaphragm disposed in its cylinder whose function is to accomplish the mixture of two or more medicinal ingredients, which are held isolated from each other by the diaphragm, when the plunger is actuated. In the Thurman reference (4,775,482), a filter sock is used to retain solid particulate filter material between the inlet and outlet of a housing so that as fluid enters the device it flows through the filter media where various lipid impurities are removed by a fat-absorbing nonionic hydrophobic resin. The Casu et al reference (4,411,796) concerns the cross-linking of polyethylenamine chains obtained by means of an alkylenediisocyanate, with the formation of transversal links of carbamic nature. The purpose of this invention is to isolate herapin from solutions containing it alone or in a mixture with other glucosamiinoglycanes. The Solowey reference (3,340,873), as noted, discloses a syringe and diaphragm arrangement for effecting the combination of two or more medicinal ingredients. These references, singly or in combination, are not concerned with and so not suggest or infer the method and apparatus of the present invention for safely preserving field water samples on site.

SUMMARY OF THE INVENTION

The present invention concerns a method and means for injecting a solution through an ion exchange filter to produce a required amount of either nitric acid, sulfuric acid or sodium hydroxide for sample collection and preservation. The invention permits a strong acid or a strong base to be safely produced at field locations in closely controlled amounts and strengths. The filter of the invention does not operate in the manner of a typical filter, since it is not used to filter a sample, but rather, for the generation of a resulting product such as an acid or base. The invention is not filtering a material, but is generating a new substance, i.e., acid or base, following the chemical reaction in a solid reagent.

In a preferred embodiment, the invention uses a strong acid ($H^+$ form) ion exchange resin or a strong base ($OH^-$ form) ion exchange resin contained in preferably a plastic syringe filter. A salt solution in the syringe is then injected through the ion exchange syringe filter producing the required needed amount of either nitric acid, sulfuric acid or sodium hydroxide for sample collection and preservation. It will be appreciated that other uses of the invention are possible in the light of the above teachings, e.g., different liquids may be injected or forced through different reagents to collect samples of other substances at locations and under circumstances where it is not feasible to transport such reagents or preserve samples on site.

BRIEF DESCRIPTION OF THE DRAWING

In the drawing, a syringe 10 and a filter cartridge 12 are shown detached for clarity, the syringe having a barrel 14 marked in cc's and a plunger 15 which includes a washer 17 and a rupturable membrane 18. The rupturable membrane 18 is positioned between the syringe 10 and the cartridge 12, and a filter 20 is contained in the cartridge which is provided with an outlet 23.

DETAILED DESCRIPTION OF THE INVENTION

Referring to the drawing, a benign salt solution (LIQUID) has been added to the syringe 10 during manufacture with a rupturable membrane 18 after which cartridge 12 is attached thereto. When plunger 15 is depressed, membrane 18 is ruptured and a selected amount of liquid 26 is forced through filter 20. The liquid passing through the filter 20 is acted upon by the reagent in the filter, and the resulting acid or base is added to the container holding the water sample to be shipped to a laboratory and stored.

Since barrel 14 is filled with a benign salt solution during manufacture, and since the reagent in cartridge 12 is an ion exchange resin, the invention eliminates the dangers inherent in transporting strong acids or bases. Samples collected for hardness, heavy metals—dissolved, suspended and total—mercury, require nitric acid. Samples collected for ammonia, nitrate, chemical oxygen demand, oil and grease, organic carbon, phenolics and phosphorous—hydrolyzable, dissolved, and total —require sulfuric acid. Samples collected for cyanides require sodium hydroxide. Dilution corrections may be made in the field or laboratory based on known volumes of the acid or base added and either the total mass or volume of the sample collected.

Since most water samples require 0.75-mL of concentrated nitric acid per 500-mL of water sample to adjust the pH to below 2, and since commercial strong acid ion exchange resins have a capacity of about 2.0-meq/mL, the volume required to generate the equivalent of 0.75-mL of concentrated nitric acid, 15.6 M, is approximately 6-mL. A volume of 2.0 meq/mL $NaNO_3$, 17%, or $KNO_3$, 20%, could be needed to run through the resin to generate a similar mass of nitric acid. Sulfuric acid may be generated by using a similar ion exchange syringe filter but using a volume of either 2.0 meg/L $Na_2SO_4$ or $K_2SO_4$. Sodium Hydroxide may be generated by using an ion exchange syringe filter that is a strong base resin. The salt solution would be either NaCL or $Na_2SO_4$.

The effectiveness of the process of the present invention on three actual samples is demonstrated as follows:

| Sample No. | I | II | III |
| --- | --- | --- | --- |
| pH | 6.38 | 8.38 | 7.48 |
| Conductivity - S/CM | 774 | 80 | 1290 |
| Carbonate - mg/L | 0 | 0.96 | 0 |
| Bicarbonate - mg/L | 156 | 35.4 | 335 |

An ion exchange bed was formed by using the barrel of a 20-mL syringe and adding a plug of glass wool followed by 10-mL of a wet common strong acid ion exchange resin having a 2.0 meq/mL exchange capacity such as Dowex HCR-W2 resin. To this was added three 20-mL portions of 5% HCl through the resin bed, the bed was rinsed with deionized water to neutral pH, then 10-mL of 17% $NaNO_3$ was added through the ion exchange bed into a 500-mL sample below. A syringe plunger was used to remove almost all of the liquid. The final pH of the water sample was measured with a pH meter with the result being a final pH of 1.9 in all three samples.

Although this invention has been disclosed and described with reference to particular embodiments, its principles are susceptible to other applications which will be apparent to persons skilled in the art. For example, a kit could be devised with the salt solution in the syringe which would be connected to the ion exchange filter. With the use of a rupturable membrane located between the syringe and filter, the acid or base would be generated by applying pressure to the plunger. Such a kit could be packaged in a plastic bubble pack for immediate use. In addition to a manufactured item in a bubble pack, the device could be reusable by using chemicals. The syringe would be filled in the laboratory with the required salt solution. A valve on the syringe would be used to hold the salt solution in the syringe. The syringe could be refilled and used many times. The ion exchange resin filter could be regenerated in the lab with either acid or base. The ion exchange resin filter could be used many times.

Among other advantages, the invention affords a safer operation over working with concentrated acid or base in the field. In kit form, the invention can be easily shipped to various locations without the inconvenience of packaging strong chemicals such as acids or bases. There is no need to begin the process by having to find a source of strong acid or base such as a chemistry laboratory. And, aprons, boots and other awkward safety equipment such as acid or base clean-up kits are not required.

Additional embodiments of the invention in this specification will occur to others and, therefore, it is intended that the scope of the invention be limited only by the appended claims and not by the embodiments described hereinabove. Accordingly, reference should be made to the following claims in determining the full scope of the invention.

What is claimed is:

1. A disposable device for producing required amounts of either an acid or base to a water sample for collection at remote locations consisting essentially of:
   a syringe having a cylindrical chamber for retaining a measured volume of a salt solution and having a discharge end;
   a plunger longitudinally movable in said chamber,
   a thin, plastic, rupturable film membrane disposed at said discharge end for sealing said syringe chamber,
   a salt solution sealed in said chamber by said plunger and said rupturable membrane therein for retaining said liquid until said plunger is actuated;
   a cartridge having an inlet end sealingly engaged with said syringe at said discharge end,
   said cartridge having an outlet end remote from said discharge end of said syringe;
   and an ion exchange filter in said cartridge adapted to react with said salt solution to produce one of an acid or base,
   whereby at said remote location said ion exchange filter can be reacted in selected amounts with said salt solution by selective depression of said plunger thereby producing a selected volume of acid or base for preservation of a water sample.

2. The device as defined in claim 1 wherein said ion exchange filter is a strong acid ion exchange resin so that when said plunger is actuated, a selected amount of said salt solution is reacted with said acid ion exchange resin to produce a selected volume of acid that is added to the collected water sample.

3. The device as defined in claim 1 wherein said ion exchange filter is a strong base ion exchange resin so that when said plunger is actuated a selected amount of said salt solution is reacted with said base ion exchange resin to produce a selected volume of base that is added to the collected water sample.

4. A method for producing required amounts of an acid or base to add to a water sample for collection at remote locations comprising the steps of:
   retaining a measured volume of a salt solution in a disposable syringe having a plunger, a cylindrical chamber, and a thin, plastic, rupturable film membrane for sealing said syringe chamber,
   applying pressure to said plunger and in turn to said salt solution and thereby bursting said film membrane sealing said syringe chamber,
   passing said salt solution through an ion exchange filter in a cartridge attached to said syringe in the discharge path of said cylindrical chamber to produce a selected volume of liquid,
   discharging selected amounts of said liquid, and adding said liquid to said water sample.

5. The method of claim 4 wherein said ion exchange filter is a strong acid ion exchange resin and said liquid produced is a selected volume of acid.

6. The method of claim 4 wherein said ion exchange filter is a strong base ion exchange resin and said liquid produced is a selected volume of base.

* * * * *